United States Patent [19]

Shanbrom

[11] Patent Number: 5,204,324
[45] Date of Patent: * Apr. 20, 1993

[54] BIOLOGICALLY COMPETENT, VIRUS INACTIVATED ALBUMIN

[76] Inventor: Edward Shanbrom, 2252 Liane La., Santa Ana, Calif. 92705

[*] Notice: The portion of the term of this patent subsequent to Jul. 7, 2009 has been disclaimed.

[21] Appl. No.: 433,605

[22] Filed: Nov. 7, 1989

Related U.S. Application Data

[63] Continuation-in-part of Ser. No. 321,522, Mar. 9, 1989, abandoned, and a continuation-in-part of Ser. No. 290,161, Dec. 28, 1988, Pat. No. 4,891,221, and a continuation-in-part of Ser. No. 276,113, Nov. 23, 1988, abandoned.

[51] Int. Cl.$^5$ .............................................. A61K 37/02
[52] U.S. Cl. ......................................... 514/2; 514/6; 514/21
[58] Field of Search ................................. 514/2, 6, 21

[56] References Cited

U.S. PATENT DOCUMENTS 5,128,150  7/1992  Shanbrom .......................... 424/533

OTHER PUBLICATIONS

Ichikawa et al.—Chem. Abst. vol. 103 (1985) p. 115,927v.
Nakano et al.—Chem. Abst. vol. 97 (1982) p. 16493b.
Pompei et al.—Chem. Abst. vol. 92 (1980) p. 122,494j.
Pompei—Chem. Abst. vol. 92 (1980) p. 104,967m.

*Primary Examiner*—Sam Rosen
*Attorney, Agent, or Firm*—Grant L. Hubbard

[57] ABSTRACT

Biologically competent non-pasteurized albumin wherein virus present in the source fluid has been inactivated with one or more of a class of compounds exemplified by glycyrrhizin, glycyrrhizinic acid or glycyrrhetinic acid glycoside, and analogous triterpenes, e.g. carbenoxolone and cicloxolone and their derivatives, and blood substitutes comprising such albumin and hemoglobin are disclosed.

20 Claims, No Drawings

BIOLOGICALLY COMPETENT, VIRUS INACTIVATED ALBUMIN

CROSS-REFERENCE TO RELATED APPLICATION

This is a continuation-in-part of my copending U.S. patent applications Ser. No. 07/321,522, filed Mar. 9, 1989, now abandoned Ser. No. 07/290,161, filed Dec. 28, 1988, now U.S. Pat. No. 4,891,221, and Ser. No. 07/276,113, filed Nov. 23, 1988, now abandoned to which priority is claimed.

FIELD OF THE INVENTION

This invention relates to the preparation of biologically component albumin wherein virus present in the source fluid has been inactivated with one or more of a class of compounds referred to here as glycyrrhizic compounds, exemplary of which are glycyrrhizin, glycyrrhizinic acid or glycyrrhetinic acid glycoside, and analogous triterpenes, e.g. carbenoxolone and cicloxolone and their derivatives.

BACKGROUND OF THE INVENTION

Cytomegalovirus (CMV) is probably the most ubiquitous of the pathogenic viruses found in animal fluids and tissues. Virtually all of the people living in the developing countries become infected with CMV early in life, and CMV infects over half the population in the developed countries of the world. CMV may remain essentially inactive in the body following an initial infection and may flare in to an active infection any time, most frequently when the body's immune system is compromised to a greater or lesser degree by disease, radiation therapy, drug therapy, surgical trauma, etc. CMV is frequently associated with, and may be a causative or contributing factor in, life-threatening disease in individuals with suppressed immune systems, and can be a principal causative factor in pneumonia, neurological disorders, febrile illness, ocular disease and hepatitis. CMV infection is a serious limiting factor in the transplantation of organs, tissues and cells and the transfusion of blood and plasma from one individual to another. The kidney transplant patient runs a high risk of contracting serious, and not infrequently fatal, CMV infection from CMV introduced by the transplant organ. Recipients of whole blood, plasma, bone marrow, cornea, cardiac, and semen run a serious risk of CMV infectious disease, the risk being multiplied whre the immune system of the recipient is suppressed to prevent rejection of the foreign organ or cells, or where immunosuppression is present from natural causes.

CMV is frequently associated with Pneumoncystis carinii and may cause or contribute to encephalitis and colitis and may be associated with Kaposi's sarcoma in AIDS patients. CMV is so ubiquitous in the blood and organs of donors who, frequently, exhibit no symptoms of infection, and its direct and contributory effects in infectious diseases is so pervasive and subtle that a CMV infection is to be presumed if another causative agent cannot be established.

There are no proven cures or generally effective drugs for the treatment of CMV infections. Certain drugs, e.g. ganciclovir, has been shown to have limited effectiveness in the treatment of certain CMV infections, e.g. CMV retinitis, but has little effect in the treatment of CMV pneumonia. Live attenuated CMV vaccine has been developed but may not protect against infection by natural CMV, and there is a real risk that the attenuated CMV may reactivate during pregnancy and infect the fetus.

While a method of preventing, or even reducing the likelihood of transmitting CMV via transfusion or transplant of organs, tissues, cells or fluids would be of enormous benefit to medical science, the present invention is not limited to treatments to inhibit CMV infection and is applicable to other classes of viruses found in animal fluids and tissues.

CMV is a member of the human herpesvirus (HV) group, which are responsible for much of mankind's discomfort and pain. The herpesviruses represent a very large, clearly defined group of viruses which are responsible for, or involved in, cold sores, shingles, a venereal disease, mononucleosis, eye infections, birth defects and probably several cancers. Three subfamilies are of particular importance. The alpha subfamily includes HV-1 (herpes virus simplex 1) which causes cold sores, fever blisters, eye and brain infections, HV-2 (herpes virus simplex 2) which cause genital ulceration, and HV-3 (HV varicella zoster) which causes chicken pox, shingles and brain infections. The beta subfamily includes HV-5, the principal member of which is CMV discussed above. The gamma subfamily includes HV-4 (Epstein-Barr) which cause infectious mononucleosis and is involved in Burkitt's lymphoma and nasopharyngeal carcinoma. Additional possibly pathogenic herpes viruses no doubt exist, one type of which, HV-6, of unknown pathogenicity has been identified. (Niederman, J. C. et al., The Lancet, Oct. 8, 1988, 817). There is evidence that the methods of this invention are effective in inhibiting the transmission of infections caused by many and perhaps all of the pathogenic herpes viruses found in animal fluids and tissues.

While blood bankers have instituted rigid criteria for exclusion of potential donors in high risk categories, this is not a satisfactory solution to the most significant threat to face the health care community in many decades. Institution of human immunodeficiency virus (HIV) testing has blood products safer, but the complete elimination of HIV contaminated blood and blood products has not been possible using present knowledge and technology. The ELISA test, for example, misses approximately 1 in 200 (0.5%) HIV infected donors, and there is no certain method for excluding donor carriers of hepatitis and other infectious viruses found in animal fluids and tissues. Increasing efforts are exerted to improve the safety of the blood supply such as retrovirus screening using surrogate markers, screening for HIV and other retroviruses with attention to population surveillance for newer agents, cleaner methods of extracting specific blood components by monoclonal antibody techniques and DNA methodologies, development of recombinant DNA products which by-pass the need for plasma derived clotting factors for administration to hemophiliacs. Careful screening of donors, followed by antibody testing, reduces the risk of AIDS and other virus-contaminated blood, but such methods are not foolproof. Such methods require testing supplies and trained technicians which are not available and are too expensive for use in such places as central Africa and other third-world countries where AIDS infects up to one-third of the population. A simpler and less costly method of handling blood is required in such areas of the world.

A photodynamic method has also been evaluated as a means of eradicating viral contaminants (Matthews, J. L. et al., *Transfusion*, 28,1 1988) but has not been proved to be generally effective and safe. While Factor VIII products may be rendered non-infectious by heat or solvent-detergent methods, no methods are known to guarantee the safety of whole blood or cellular components or plasma. For the whole blood recipient, however, the only reasonably reliable safety procedures are programs allowing for self donation prior to elective surgery by the donor and the use of blood from designated donors, but such programs are incredibly difficult logistically. In spite of heroic efforts to meet the challenge of virus contaminated blood supply, an imperative need continues to exist for a method for treating whole blood for use in transfusion. It is apparent from the foregoing discussion that a method of killing or inactivating pathogenic viruses in organs, tissues, cell and fluids intended for transfusion or transplantation would be an enormous advance in medicine. It is to this major national and worldwide health care challenge that the present invention is directed.

Glycyrrhizic acid, 20B-carboxy-11-oxo-30-norolean-12-en-3B-yl-2-O-B-D-glucopyranuronsyl-α-D-glucopyranosiduronic acid, commonly known as glycyrrhizin, glycyrrhizinic acid or glycyrrhetinic acid glycoside (also referred to as biosone, enoxolone, and glycyrrhetin) an extract from Glycyrrhiza, better known as licorice, an extract of the dried rhizome and roots of Glycyrrhiza glabra, is a triterpene and is exemplary of the triterpenes to which this invention relates. Analogous triterpenes to which this invention relates include carbenoxolone and cicloxolone. This invention thus relates to glycyrrhizic acid and analogues thereof, in the form of acids, salts, esters and other derivatives. Many such derivatives are known, such as, for example, glycyrrhetinyl stearate; monopotassium glycyrrhetin; potassium glycyrrhetinate; 11-deoxoglycyrrhetinic acid hydrogen maleate sodium salt; α-D-glucopyranosiduronic acid monoarginine glycyrrhizinate; 18α-Glycyrrhizic acid monosodium salt; 18-α-Glycyrrhizic acid monopotassium salt; disodium 18-α-glycyrrhizate; glycyrrhizinc acid mono(triethanolamine) salt; trisodium glycyrrhizinate; sodium glycyrrhizate; ammonium glycyrrhizinate; sodium carbenoxolone (biogastrone; glycyrrhetinic acid hydrogen succinate disodium salt); and acetylglycyrrhetic acid (glycyrrhetinyl acetate). Glycyrrhizin and the virucidal analogues and derivatives thereof are referred to for convenience herein as glycyrrhizic triterpenoids abbreviated GTPD. Presently the principal GTPD compounds of interest are glycyrrhizin (coded TPD-1 in some of my work), carbenoxolone (coded TPD-2 in some of my work) and cicloxolone.

Ring-substituted derivatives of GTPD compounds are contemplated and are included in this invention. Halogen ring substituents, such as, for example, fluoro- and chloro-substituents, sulfate and other active and/or inactivating substituents to the ring structure of GTPD compounds are specifically included in this invention, without excluding other ring-substituted derivatives of GTPD compounds.

In addition to its use as a flavoring agent, licorice has long been a common folk medicine for the treatment of sore throats. While not widely known, various extracts of and preparations derived from licorice, e.g. glycyrrhizin and its derivatives, principally the salts of glycyrrhizic acid, have also been used to a limited degree for many years as an orally administered medication for the treatment of peptic ulcers (Chandler, R. F., *Can. Pharm. J.*, V118, No. 9, 1985), and oral administration of glycyrrhizin contemporaneously with saponin antiinflamatory agents has been reported to inhibit saponin and saponigen hemolysis (Segal, R. et al., *Biochem. Pharmacol.* 26, 7 1977).

GTPDs have been evaluated extensively in vitro, and have been administered orally, intramuscularly and intravenously. No significant toxicity from limited, short term administration of glycyrrhizin has been reported. Adverse reactions have been reported in certain instances of prolonged oral ingestion and a slight relapse after rapid discontinuation of intravenous administration of Stronger Neo-Minaphagen C (SNMC) solution, glycyrrhizin (0.2%), cysteine(0.1%) and glycine (2%) was attributed to the steroid ring in glycyrrhizin (Fujisawa K. et al., *Asian Med. J.* (Japan), 23, 10 1980). Dosages of SNMC as high as 60 ml/day (~12 mg/dy of glycyrrhizin) have been reported (Iwamura K., *Therapiewoche* (W. Germany) 30,34 1980).

Inactivation of viruses, in vitro, under certain conditions, has been reported (see, e.g., Pompei R., *Exprientia* (Switzerland) 36/3 1980). Such anti-viral activity as GTPD compounds sometimes exhibit has been attributed to reverse transcriptase-inhibitory activity (Nakashima, H. et al., *Jpn. J. Cancer. Res.* 78,8 1987) and to enhancement of interferon-gamma production (Shinada, M. et al., *Proc. Soc. Exp. Biol.* 181,2 1986), but the exact mechanism of the anti-viral function has not been confirmed.

Dargan, D. J., and Subak-Sharpe, J. H., (*J. Gen. Virol.*, 1985–1986) reported antiviral action of carbenoxolone and cicloxolone on herpes simplex virus. Their dose-response experiments showed cicloxolone sodium or carbenoxolone sodium interfered with the HSV replication cycle and reduced the infectious virus yield by 10,000- to 100,000-fold, cicloxolone being the more potent anti-herpes agent, but no consistent effect on HSV DNA synthesis was identified. Some inhibition of cellular DNA synthesis was observed, but this was relatively slight.

Csonka, G. W. and Tyrrell, D. A. (*Br. J. Vener. Dis.* 1984, 60 (3) p178) undertook a double blind clinical study to compare the efficacy of carbenoxolone and cicloxolone creams with placebo in initial and recurrent herpes genitalis and reported significant differences in the time to disappearance of pain and the healing of lesions using cicloxolone, but carbenoxolone showed insignificant beneficial effect.

GTPDs have also been evaluated therapeutically as anti-viral agents in the chemotherapy of acquired immune deficiency syndrome (AIDS) (Ito, M., Yamamoto, N., *Yakaguaku Zasshi* (Japan) 188,2 1988), treatment of Epstein-Barr virus (EBV) infections (Van Benschoten, M. M., *Am. J. Acupunct*, 16,1 1988), and in the treatment of chronic hepatitis (Fujisawa, K. et al., *Asian Med. J.* (Japan), 23,10 1980).

The anti-viral activity of GTPDs varies so unpredictably as to preclude any generalized statements as to whether such compounds have general anti-viral effect or even as to whether such compounds will generally have anti-viral value as to any given virus or in unproven milieus.

The major constituent of plasma is albumin whose primary role is that of osmotic regulation; it is responsible for 75–80% of the osmotic pressure of plasma. Albumin also serves important roles in the transport of small molecules such as drugs.

An important feature which segregates albumin from other colloids as well as crystalloids is its unique ability to bind reversibly with both anions and cations; hence, albumin can transport a number of substances including fatty acids, hormones, enzymes, dyes, trace metals, and drugs. Substances which are toxic in the unbound or free state are generally not toxic when bound to albumin. This binding property also enables albumin to regulate the extracellular concentration of numerous endogenous as well as exogenously administered substances.

Albumin in general has three types of binding sites (one for acidic, one for basic, and one for neutral compounds), and it plays a critical role in the binding and transport of lipid and lipid-soluble material. Albumin binds with and transports many administered drugs. Because of the phenomenon of mutual displacement of similar type substances, adverse drug interactions may occur. This phenomenon may have important ramifications during disease states such as sepsis, burn injury, and circulatory shock due to a number of etiologies, especially in conjunction with treatment with drugs which may be toxic at high concentrations.

Human serum albumin is believed to be a scavenger of oxygen-free radicals, an important phenomenon which also extends to scavenging of radicals required for lipid peroxidation.

Preliminary work in the endotoxemic sheet adult respiratory distress syndrome (ARDS) model also demonstrated that pretreatment with human serum albumin markedly attenuates the 300% to 400% increases in pulmonary lymph flow, transvascular protein clearance, and transvascular protein flow which normally occurs during endotoxemia. UNIQUE FEATURES OF ALBUMIN: A BRIEF REVIEW, Thomas E. Emerson, Jr., Ph. D., *Critical Care Medicine*, Vol. 17, No. 7 (1989).

Treatment with human serum albumin to bind toxic products generated during inflammatory disease states has not received widespread attention. However, a few studies and the inherent ability of albumin to bind with numerous toxic plasma substances support the concept.

Albumin is critical for the transport of numerous compounds, especially non-water soluble ones. It binds with iron and lipids and other potentially toxic substances, e.g., bilirubin. Thus albumin acts as a buffer to prevent increases in potentially cytotoxic endogenous lipid-soluble substances by binding with, and thus limiting, increases in plasma and interstitial fluid concentrations of these substances.

In addition to displacement of an albumin-bound drug by another, endogenous substances may also alter significantly the unbound or "free" plasma and interstitial fluid concentration of a drug. For example, as the concentration of bilirubin increases in certain disease states, a drug which occupies the same binding site as bilirubin will be displaced by the bilirubin, and the plasma concentration of the free drug will increase, possibly to toxic levels. Also, as the plasma concentration of albumin decreases, the plasma and interstitial fluid concentration of the unbound (free) drug will increase.

Plasma albumin concentration is usually decreased to varying degrees in disease states such as sepsis, burn injury, and circulatory shock. Resuscitation with large volumes of non-albumin colloid or crystalloid solutions will further decrease an already low albumin concentration and may consequently further limit the ability of albumin to modulate the free concentration and transport of toxic substances or drugs administered for therapeutic purposes.

Another feature of albumin is its inhibitory effect on pathologic platelet aggregation, which may be due to a greater affinity of arachidonic acid for albumin than for platelet-generated cyclooxygenase. It has also been demonstrated that albumin enhances the inhibition of factor Xa by antithrombin-III (AT-III).

In addition to the well-known role of albumin in generating colloid osmotic pressure, it also may protect the lung and other organs from edema by preserving microvascular integrity.

Very recent work support a role for albumin in the maintenance of normal microvascular permeability to protein.

It is known that albumin binds to glycyrrhizic triterpenoids. Carbenoxolone is a potent ulcer-heating drug which is extensively bound to plasma proteins and therefore has the potential for displacement interaction. Carbenoxolone has been shown to be bound to human serum albumin in vitro at a different class of binding site to many other drugs and does not potentiate the pharmacological activity of warfarin, tolbutamide, chlorpropamide or phenytoin in the rat. Thornton PC; Papouchado M; Reed PI *Scand J Gastroenterol Suppl* 1980, 65 p35-9

The binding of glycyrrhizin to human serum and human serum albumin (HSA) was examined by an ultrafiltration technique. Specific and nonspecific bindings were observed in both human serum and HSA. The association constants (K) for the specific bindings were very similar: $1.31 \times 10^5$ $M^{-1}$ in human serum and $3.87 \times 10^5$ $M^{-1}$ in HSA. Glycyrrhizin binds to only the albumin fraction. It was concluded that the glycyrrhizin-binding sites in human serum exist mainly on albumin and glycyrrhizin binds to specific and nonspecific binding sites at lower and higher concentrations than approximately 2 mM, respectively. Ishida S; Sakiya Y; Ichikawa T; Kinoshita M; Awazu S, *Chem Pharm Bull* (Tokyo) 37 (1). 1989. 226-228.

Comparison by equilibrium dialysis of plasma protein binding sites for carbenoxolone in people under 40 yr of age and in people over 65 yr of age showed that the number of binding sites was reduced in the elderly and that this fall was associated with a reduction in plasma albumin levels. Hayes M J; Sprackling M; Langman M, *Gut* 18 (12) 1977 1054-1058.

Albumin has been used as an emulsion stabilizer oil-and-water emulsion injectable medical preparations, e.g. fluoribiprofen, Mizushima et al, U.S. Pat. No. 4,613,505, Sept. 23, 1966; as a binding molecule for tryptophan, Pollack, U.S. Pat. No. 4,650,789, Mar. 17, 1987; with chemical modification as complexing agents for cholesterol derivatives, Arakawa, U.S. Pat. No. 4,442,037, Apr. 10, 1984; as conjugates with enzyme chemically linked to an antibody, Poznansky, U.S. Pat. No. 4,749,570, Jun. 7, 1988; and as chemically coupled conjugates of leukotrienes, Young, et al, U.S. Pat. No. 4,767,745, Aug. 30, 1988.

Human serum albumin is a remarkable protein which performs numerous tasks critical to maintenance of the milieu interieur. The best known functions of albumin involve regulation of transvascular fluid flux and hence, intra and extravascular fluid volumes and transport of lipid and lipid-soluble substances. However, it is also involved in a number of other vital functions, some of which have only recently been suggested and perhaps others which are as yet unrecognized. Among recognized unique features of albumin are: a) binding, and hence, inactivation of toxic products; b) regulation of the plasma and interstitial fluid concentrations of endogenous and exogenously administered substances and drugs; c) involvement in anticoagulation; d) maintenance of microvascular permeability to protein; and e) scavenging of free radicals and prevention of lipid peroxidation. This latter property may prove to be critically important, particularly in inflammatory disease states in which free radicals are thought to be a major culprit in direct damage due to tissue oxidation and indirect tissue damage due to inactivation of important antiproteinases such as $a_1$-PI and AT-III. See UNIQUE FEATURES OF ALBUMIN: A BRIEF REVIEW, Thomas E. Emerson, Jr., Ph.D., *Critical Care Medicine*, Vol. 17, No. 7 (1989).

Procedures for large-scale, i.e. at least one unit of blood, fractionation of whole blood into its component cell types and plasma, and methods for the preparation of isolated plasma protein fractions from plasma are well-known. The principles of enhanced sedimentation, e.g. centrifugation, and adhesion can be used to separate anticoagulated whole blood into platelet concentrate, leukocyte concentrate, packed red cells or leukocyte-poor packed red cells, and platelet-rich or platelet-poor plasma. Techniques based upon these principles are available for the selective isolation of platelets (plateletpheresis), leukocytes (leukapheresis), and plasma (plasmapheresis), and for the separation of different leukocyte cell types (granulocytes, lymphocytes, and monocytes).

Methods are known for the fractionation of plasma into the commonly used therapeutic plasma protein preparations: albumin; antihemophilic factor; fibrinogen; immune serum globulins (both normal and specific); plasma protein fraction; and prothrombin complex. The most commonly used fractionation procedures involve the techniques of cold ethanol or polyethylene glycol precipitation, heat denaturation, and ion-exchange chromatography.

Hazards of viral hepatitis or pyrogen contamination of plasma fractions do exist, and precautions must be taken to minimize these risks.

Two methods have been used to classify the plasma proteins. The first method is based upon solubility in salt solutions. On this basis there are three categories: (1) euglobulins, those proteins insoluble in water at their isoelectric point and precipitated by 33% saturated (1.3M) ammonium sulfate; (2) pseudoglobulins, those proteins soluble in water at their isoelectric point and precipitated at ammonium sulfate concentrations between 33% and 48% saturation (2M); and (3) albumins, those proteins soluble in water at their isoelectric point and requiring ammonium sulfate concentrations greater than 50% saturation (2.06M) for precipitation. The second classification method is based upon electrophoretic mobility. The Schlieren pattern obtained from free boundary electrophoresis of normal human plasma has 6 peaks. The pattern obtained with normal human serum has 5 peaks. Each peak represents a family of proteins having similar electrophoretic mobility. By precipitating all proteins insoluble in 50% saturated ammonium sulfate, the fastest moving peak was identified as albumin. The peak present in plasma but absent in serum was identified as fibrinogen. The remaining peaks were identified as globulins and named ALPHA 1-, ALPHA 2-, BETA-, and GAMMA -globulins in order of decreasing mobility. Each of these classifications represents a heterogeneous mixture of proteins grouped on the basis of solubility or electrophoretic mobility.

The plasma proteins serve a wide variety of functions in the human organism. Their roles in the maintenance of blood volume and other physical characteristics of blood, such as viscosity, are extremely important because blood, in order to perform any of its numerous functions, must be a rapidly circulating medium. If the volume of plasma falls, the pumping action of the heart is strained and there is increased resistance to flow owing to the increased concentration of the red cells relative to the plasma. The blood volume depends on the balance between the hydrostatic pressure of the blood in the capillaries, which tends to expel liquid from the blood into the tissues, and the osmotic pressure (owing to the plasma proteins), which tends to draw liquid back into the blood. The major contribution to the osmotic pressure of plasma is from albumin because of its concentration and properties.

Albumin comprises more than 50% of the plasma proteins by weight. It has a relatively low molecular weight and a high net negative charge at physiological pH. Albumin solutions have relatively low viscosity because of the spherical shape of the molecule. The major impetus for the development of fractionation methods was the need to provide large amounts of a blood volume expander for the treatment of battlefield injuries during World War II. A product was desired that would provide the required oncotic action, not require refrigeration, and be free from the transmission of disease. Human albumin was found to be the most acceptable therapeutic fraction. A fractionation method was developed during the 1940s by a group headed by Cohn at the Harvard Medical School. The procedures were scaled up at the Harvard pilot plant and made available to commercial laboratories under contract to the U.S. Navy to provide blood derivatives for the Armed Forces. The methods developed during this period, with some modifications, are still the most popular methods for the preparation of albumin and ISG.

Cohn and co-workers described methods for the separation and purification of the protein and lipoprotein components of human plasma. In each of these methods there was an initial separation of the protein components of plasma into a small number of fractions in which the major components are separated, and then into a large number of subfractions into which these components are further concentrated and purified. The methods involved lowering the solubility of proteins by reducing the dielectric constant of the solution by the addition of ethanol. Thus separations could be carried out in the range of low ionic strengths at which the interactions of proteins with electrolytes differ from each other markedly. The protein to be separated must have a high solubility when most other components of the system have low solubilities, or the converse.

The plasma used in the development of these methods was obtained from blood collected into sodium citrate anticoagulant. Acetate and carbonate buffer systems were used to adjust pH and ionic strength. Precipitation was carried out at the lowest convenient ethanol concentration and temperature, and at the optimum pH and ionic strength for each separation.

Although the fractional precipitation methods described above were found to be adequate for the purpose of producing large amounts of therapeutic concentrates of plasma proteins, a new procedure took advantage of the increased stability of proteins in the solid state. All of the proteins are rapidly precipitated by a combination of the effects of ethanol and zinc ion. Separations from the solid state are made by fractional extraction. Specific metal-protein interactions favor the separation of undenatured proteins by reducing the extremes of pH and ethanol concentration. The lowest pH used is 5.5 and the highest ethanol concentration is 19%. This method, in its entirety, has never been put into large-scale use. The use of 95% ethanol reduces the amount of ethanol required and reduces the volume of solutions to be processed.

For many therapeutic indications a preparation called plasma protein fraction (PPF) is used interchangeably with albumin. PPF is albumin in a slightly less pure form than the albumin produced by the methods described above. The contaminants are ALPHA-and BETA-globulins and salts. PPF can be produced by eliminating precipitation IV4 and precipitating fractions IV4 and V in a single step. If this is done, a filtration of supernatant phase IV1 is required. PPF is more economical to produce than albumin and can be recovered in higher yield. All immune serum globulin (ISG) for therapeutic use is prepared from large pools of plasma from many donors so that the final product will contain a broad spectrum of antibodies.

Alternative methods for the production of albumin and ISG are also known. An economical method for the preparation of albumin involves heat denaturation of the nonalbumin components of plasma. In this method, plasma or serum is heated to 70° C. in the presence of caprylate ions, under which conditions the globulins and fibrinogen become denatured. The caprylate serves to stabilize the albumin against thermal denaturation. By manipulation of pH, all the denatured proteins are precipitated and removed, leaving albumin in solution.

A modified method for the production of albumin by the heat denaturation of the nonalbumin components has also been developed. This method allows for the separation of the coagulation factors and ISG, if they are desired, whereas the isolation of albumin can begin at any step. The albumin produced is further concentrated by polyethylene glycol precipitation or ultrafiltration. Several methods have been used for the preparation of heat stable plasma fractions rich in albumin, to be used as plasma volume expanders.

Zinc complexes have also been used for fractionation, a fraction obtained by desalting plasma with ion-exchange resins and thus precipitating euglobulins, has been described and fractionation scheme using polyphosphate as a precipitant has also been used. None of these methods yield a fraction with a sufficiently high albumin content to meet regulations of the FDA for albumin or plasma protein fraction (PPF). Polyethylene glycol (PEG) has become a very popular protein precipitant. It acts by concentrating the protein component in the inter-PEG spaces by a displacement mechanism.

Plasma fractionation schemes using precipitants other than ethanol or PEG for the isolation of albumin and ISG have been developed and used successfully, primarily in Europe. Ethyl ether has been used as a precipitant in England. Rivanol and ammonium sulfate have been used in Germany and, in France, placental blood is fractionated with the use of chloroform, trichloroacetic acid, and ethanol as precipitants. Recently, Pluronic polyols (BASF Wyandotte Corp) and solid-phase maleic anhydride polyelectrolytes have been used successfully on an experimental scale.

Adsorption chromatography has been used for the purification of ISG. A large-scale method for the production of albumin utilizing PEG, adsorption chromatography, and gel chromatography has recently been developed. Continuous preparative electrophoresis, polarization chromatography, isotachophoresis and isoelectric focusing are all promising techniques for the large-scale purification of plasma proteins.

The major hazard in producing fractions from large pools of plasma is the transmission of virus, the most serious, being hepatitis. This is a danger both for the recipient of the fractions and for the workers in fractionation plants. It has been shown that fractionation workers, particularly those engaged in the preparation of plasma pools, are at high risk of developing hepatitis B. The high risk products are fibrinogen, AHF, and prothrombin complex. The low risk products are ISG, PPF, and albumin. The lack of infectivity of PPF and albumin is attributable to heating the final products at 60° C. for 10 hours.

It is now required in the United States that all donors of blood or plasma be tested for the presence of hepatitis B surface antigen by radioimmunoassay or reversed passive hemagglutination. This screening reduces but does not pervent the transmission of hepatitis B virus. A major problem is the transmission of non-B hepatitis, for which there is no screening test. Recent evidence indicates that non-A, non-B hepatitis also invokes a viral agent.

Another hazard of plasma fractionation is the partial denaturation of some fractions such as ISG, caused by the fractionation methods. These denatured proteins may have toxic effects or may be immunogenic in the recipients. Among these undesirable side effects is the significant degree of loss of biological competence and the loss or blockage of many binding sites on albumin are lost by the inherent denaturation resulting from this pasteurization or heating process. According to present technology, the disadvantages of denaturation are more than compensated for by the increased stability and potency of concentrated fractions, but there remains a great need for more biologically competent albumin which is free of the hazards and risks of virus infections.

SUMMARY OF THE INVENTION

It has now been discovered that albumin binding to glycyrrhizin, glycyrrhetinic acid, carbenoxolone and cicloxolone and the analogues thereof does not reduce, and generally to enhances, the viral inactivation power of glycyrrhizic triterpenoid compounds and that a non-viral infectious albumin which is more biologically active than albumin produced in accordance with the prior art results by viral inactivation with glycyrrhizic triterpenoid compounds, referred to hereinafter as GTPD's or GTPD compounds.

It has now been discovered that combinations of GTPD compounds with albumin (GTPD-Albumin) exhibit striking and most unexpected advantages in viral inactivation.

Viral inactivation, as used here, means rendering the virus non-infective, i.e. the virus does not induce disease in a patient. In most instances traditional methods of quantifying virus population growth and reduction, e.g. log kill (See Fraenkel-Conrat, H., Kimball, P. C., and Levy, J.A. *VIROLOGY*, Second Edition, Prentice Hall, Englewood Cliffs, N.J., 1988, and Jakoby, W. H. and Pastan, I. H. (Eds), CELL CULTURE, (Volume LVIII of "Methods in Enzymology", Academic Press, Inc., New York, Chapter 11) are good indicators of viral inactivation. However, viral inactivation is accomplished by GTPD-Albumin beyond the log kill measurement since any remaining virus are incapable of infecting a patient and are incapable of replicating.

At least one of the retroviridae is susceptible to the treatment of this invention, according to presently available data. The most notorious of the retroviridae, HIV-1, the only virus thus far identified as inducing AIDS in humans, is inactivated and/or killed using the methods and compositions of this invention. Other retroviridae are considered to be susceptible to the present invention, and treatment to prevent transmission of retrovirus-infected organs, tissues, cells and fluids is within the scope of this invention.

DESCRIPTION OF THE PREFERRED EMBODIMENT

Particularly striking results are accomplished using albumin which has not been stabilized in the traditional way, e.g. with caprylate, and has not been heated. According to the prior art, such an albumin product would be regarded as unsafe because of the potential presence of pathogenic virus. If, however, the stabilization step and the heating step are replaced by the addition of GTPD to the albumin, the virus are inactivated and the albumin is biologically competent. GTPD-Albumin formed in this manner has higher biological activity than GTPD-Albumin prepared from conventional albumin.

The dramatic and unpredictable increase in antiviral activity of GTPD-Albumin prepared from unpasteurized (not heat treated to inactivate virus) albumin was demonstrated in a test using a VSV/BVD sensitive cell line performed when the cells were in log phase, the samples were inoculated with $10^9$ pfu of vesicular stomatitis virus (VSV), incubated overnight and serially diluted in MEM with 10% FBS (fetal bovine serum), and then inoculated with VSV. The 0.10% GTPD (carbenoxolone) alone and 0.10% GTPD (carbenoxolone) in 5% solutions of various albumins were introduced at dilutions of from $1:10^2$ to $1:10^9$. The cells were examined daily for five days for virus caused CPE. following table summarizes the comparative results.

| LOG KILL OF VSV BY TPD | |
|---|---|
| Albumin Used | Log Kill Five Days |
| None | 4.6 |
| Baxter Buminate ® (USP Lot 2746M011AA) | 1.3 |
| Miles Human Albumin Fatty Acid Free (Lot 82-324) | 1.6 |
| Hyland IS 9988 Human Albumin | 2.0 |
| Non-Stabilized, non-pasteurized solvent detergent albumin[1] | 5.6+ |

[1]Human serum albumin prepared by Cohn Fractionation. Solvent-Detergent precipitation and alcohol ultrafiltration, not heated and no stabilizer, e.g. caprylate or tryptophan, added.

It should be noted that at extreme dilutions of GTPD, binding to albumin may actually reduce antiviral activity; however, higher concentrations of GTPD can be used and the viral inactivation is not decreased even with the least biologically competent albumin and enhancement is generally observed.

Non-stabilized, non-heated albumin is, however, vastly superior to "conventional", i.e. stabilized and pasteurized, albumin, presumably because of a greatly increased ability to form GTPD-Albumin as a result of greater biological competence. Even at extreme dilution, an approximately 6 log kill was found. At lower dilutions (higher concentrations of GTPD) the kill was apparently complete, probably 7 to 9 logs.

It has also been found that the deactivation of antiviral power of GTPD by lipoproteins and/or fatty acids is eliminated or greatly reduced by adding the GTPD as GTPD-Albumin.

The ability of albumin to (a) bind GTPD, (b) not reduce and generally to enhance the viral inactivation power of GTPD, and (c) eliminate at low concentrations or greatly reduce any tendency of GTPD to hemolyze red blood cells is of enormous import. These results means that GTPD can be carried into the system via albumin without losing its viral inhibition power, can be used at much higher concentrations than would otherwise be possible, and can be used where hemolysis is unacceptable.

As reported in the prior art, it is known that GTPD will bind to albumin. The nature of the binding, which results in GTPD-Albumin, is not fully understood. GTPD bound to albumin would be expected to be less active chemically and biologically. Quite surprisingly, however, it was found that the viral inactivation characteristics of GTPD bound to albumin were not only not decreased but were, in some instances at least, enhanced. Perhaps the most interesting discovery, however, was that the tendency of GTPD to lyse erythrocytes at high concentrations of GTPD in blood or packed red blood cells was greatly reduced. At lower concentrations, GTPD, alone, actually stabilized red blood cells but at higher concentrations, GTPD tended to lyse red blood cells. This made it necessary to work with GTPD concentrations in blood and blood products within a fairly narrow range. GTPD can, however, be added to blood as GTPD-Albumin at two to five times the concentration which would lyse cells if the GTPD had been added alone with no discernable lysing of RBC. This permits the use of higher concentrations of GTPD, with more certainty of virus inactivation and less risk of lysing during mixing. GTPD-Albumin prepared from non-stabilized, non-heated albumin has even less tendency to hemolysis than GTPD-Albumin prepared from conventional albumin. Virus-inactivation by GTPD-Albumin from non-stabilized, non-heated albumin was also higher than that of GTPD-Albumin from conventional albumin. For example, a 5–6 log (complete) kill of vesicular stomatitis virus (VSV) in packed red blood cells was accomplished by adding GTPD-Albumin solution to give a GTPD concentration of 0.5% carbenoxolone and 10% albumin after a wait period of one hour at 45° C. without significant hemolysis.

There is no criticality as to the ratio of GTPD and albumin. Generally, however, albumin will be present, on a weight percent basis, in ratio of from about 5:1 to 100:1, or more. For example, GTPD will generally be in the concentration range of about 0.0001 to about 10 w/%, preferably in the range of from about 0.05 wt % to about 3 wt %, in the albumin.

Albumin fully saturated with one or more glycyrrhizic triterpenoid compounds is conveniently prepared from human serum plasma simply by adding GTPD to the HSA and recovering the precipitate which consists essentially of albumin saturated with the GTPD. The albumin thus prepared will not be highly pure, but will free of infectious virus and is quite suitable for many uses. For example, such a biologically competent, infectious virus-free albumin may be used in the preparation of blood substitutes by adding hemoglobin, and such other compounds as may be desired, using the GTPD-Albumin as the carrier for the hemoglobin. will be in the concentration range of from about 0.25 wt/% to 15 wt/%. It is convenient to prepare a near saturate solution of albumin and add the maximum load of GTPD which the solution will carry as GTPD-Albumin and dilute the solution as desired.

The GTPD-albumin compositions of this invention may be added to conventional anticoagulants, e.g. citrate dextrose, citrate phosphate dextrose, EDTA, heparin, etc. to enchance the anticoagulant effect of these, or to replace, in whole or in part, such anticoagulants.

Of the readily available GTPD compounds, carbenoxolone is preferred for its anti-viral effectiveness; however, glycyrrhizin and cicloxolone, in particular, and other GTPD compounds may be used with various advantages depending upon the particular compound.

When GTPDs are added to whole human blood containing substantial amounts of lipids and lipoproteins the GTPD's are, over a period of time, absorbed or absorbed or otherwise removed from solution as active compounds. The GTPD compounds when added as GTPD-Albumin, however, remain in the blood as effective viral inactivators for a much longer period of time, as compared with GTPD added alone.

The GTPD compounds may be used to form GTPD-Albumin in their acid form; however, it is always necessary to check the pH after adding the GTPD compound and, if necessary, adjust the pH to about 7.0–8.0, e.g. with NaOH or KOH, before using the albumin solution, as certain acid form GTPD compounds drop the pH of plasma significantly to the pH 4–5 range.

The acid form of the GTPD compounds is only slightly soluble in water but is quite soluble in glycerol, alcohol, dimethyl sulfoxide and other organic solvents. The salt, e.g. ammonium, sodium or potassium salts, of the GTPD compounds are, generally, soluble in water, the sodium and potassium salts being more soluble than the ammonium salts. It is, thus, convenient to purchase or prepare the GTPD compounds as sodium or potassium salts.

The effectiveness of GTPD compounds in killing or inactivating virus has been verified in fetal bovine serum (FBS) where additions glycyrrhetinic acid in concentrations of 0.05 to 0.7 percent followed by adjustment to pH 6.5 and 7.4, respectively for various trials, established a 100% kill of the relatively resistant vesicular stomatitis virus (VSV) was accomplished in all cases.

The invention is embodied in an article of commerce consisting essentially of non-pasteurized albumin and containing one or more glycyrrhizic triterpenoid compounds in an amount of from 0.0001 to 10 wt/ %, preferably from about 0.05 to about 3 wt/ %. The term "consisting essentially" is used generally in its conventional sense, namely (as applied to the GTPD-Albumin) that the principal gross biological characteristics of the composition are determined by the albumin, but that other materials which do not destroy or materially change such biological characteristics may be present; indeed, fundamental to many important uses of the GTPD-Albumin is its ability to serve as a carrier, buffer, osmotic control agent, etc., for other biologically active species. The term "non-pasteurized" is, likewise, used generally in the sense which would usually be attributable thereto, namely, that the albumin has not been heat treated to remove microorganism contamination with the resulting partial denaturization which inherently results from such heat treatment. Since the heat treatment is avoided, stabilizers such as caprylates or tryptophans need not be added.

It is, however, entirely feasible to maintain the mixture of albumin and glycyrrhizic triterpenoid compound at a temperature of 37°±7° C., typically in the range of 37° to 45° C. for a period of at least about one hour or longer to assure virus inactivation. Treatment at these low temperatures does not denature the albumin.

The invention is also embodied in a method of preparing albumin comprising the steps of separating serum from blood and concentrating or isolating albumin from the serum without heat inactivation of virus and inactivating virus by mixing such albumin with one or more glycyrrhizic triterpenoid compounds in a concentration of from 0.0001 to 10.0 wt/ %, preferably from about 0.5 to about 3 wt/ %, based on albumin, sufficient to substantially inactivate susceptible virus. Conventional separation and concentration steps, e.g. the Cohn fractionation method, alcohol ultrafiltration, butanol and ether extraction, column procedures, etc. may be used to obtain albumin of the purity desired, but without the application of a heating step to inactivate virus which partially denatures the albumin.

Industrial Application

This invention has direct application in the blood fractionation and blood derivative industries.

What is claimed:

1. A therapeutic composition of matter consisting essentially of non-pasteurized biologically competent human albumin substantially separated from plasma and other blood components, substantially free of stabilizers and free of active virus and suitable for human therapy, containing one or more glycyrrhizic triterpenoid compounds.

2. A therapeutic composition of matter consisting essentially of non-pasteurized biologically competent human albumin substantially separated from plasma and other blood components, substantially free of stabilizers and free of active virus and suitable for human therapy, containing one or more glycyrrhizic triterpenoid compounds in an amount of from 0.0001 to 10 wt/% based on human albumin effective to inactivate susceptible viruses found in fluids from which the human albumin was derived.

3. The non-pasteurized albumin of claim 2 wherein the concentration of glycyrrhizic triterpenoid compounds is from about 0.05 wt % to about 3 wt %.

4. A method for preparing biologically competent, virus inactivated human albumin suitable for human therapy comprising mixing a concentrate of human albumin, said albumin being substantially separated from plasma and other blood components, substantially free of stabilizers and which has not been pasteurized; with one or more glycyrrhizic triterpenoid compounds the resulting albumin composition comprising, during preparation, an amount between 0.0001 and 10 weight percent of glycyrrhizic triterpenoid compound sufficient to inactivate pathogenic virus therein.

5. A method for preparing biologically competent, virus inactivated human albumin suitable for human therapy comprising mixing a concentrate of human albumin, said albumin being substantially separated from plasma and other blood components, substantially free of stabilizers and which has not been pasteurized; with one or more glycyrrhizic triterpenoid compounds in a concentration of from 0.0001 to 10.0 wt/% based on human albumin sufficient to substantially inactivate susceptible viruses.

6. The method of claim 5 wherein the glycyrrhizic triterpenoid compounds is present in a concentration of from about 0.05 to about 3 wt/% in the human albumin.

7. Blood substitute consisting essentially of hemoglobin and non-pasteurized human albumin, said albumin being substantially separated from plasma and other blood components, substantially free of stabilizers and being suitable for human therapy, containing one or more glycyrrhizic triterpenoid compounds the albumin composition comprising, during preparation, an amount between 0.0001 and 10 weight percent of glycyrrhizic triterpenoid compound sufficient to inactivate pathogenic virus therein.

8. Blood substitute consisting essentially of hemoglobin and non-pasteurized human albumin, said albumin being substantially separated from plasma and other blood components, substantially free of stabilizers and suitable for human therapy, containing one or more glycyrrhizic triterpenoid compounds in an amount of from 0.0001 to 10 wt/% effective to inactivate susceptible viruses found in fluids from which the human albumin was derived.

9. Blood substitute comprising hemoglobin and non-pasteurized albumin containing one or more glycyrrhizic triterpenoid compounds in an amount of from 0.0001 to 10 wt/% effective to inactivate susceptible viruses found in fluids from which the albumin was derived.

10. The blood substitute of claim 9 wherein the concentration of glycyrrhizic triterpenoid compounds is from about 0.05 wt % to about 3 wt %.

11. A method for preparing blood substitute comprising (a) mixing together hemoglobin, (b) biologically competent, virus inactivated human albumin, said albumin being substantially separated from plasma and other blood components, substantially free of stabilizers, which has not been pasteurized and which is suitable for human therapy, the albumin composition comprising, during preparation, an amount between 0.0001 and 10 weight percent of glycyrrhizic triterpenoid compound sufficient to inactivate pathogenic virus therein and (c) one or more glycyrrhizic triterpenoid compounds.

12. A method for preparing blood substitute comprising mixing together (a) hemoglobin, (b) biologically competent, virus inactivated human albumin, said albumin being substantially separated from plasma and other blood components, substantially free of stabilizers, which has not been pasteurized and which is suitable for human therapy and (c) one or more glycyrrhizic triterpenoid compounds in a concentration of from 0.0001 to 10.0 wt/% sufficient to substantially inactivate susceptible viruses.

13. The method of claim 12 wherein the glycyrrhizic triterpenoid compounds is present in a concentration of from about 0.05 to about 3 wt/%.

14. A method of preparing a therapeutic composition of matter consisting of human albumin suitable for human therapy substantially saturated with one or more glycyrrhizic triterpenoid compounds comprising the steps of:
  adding one or more glycyrrhizic triterpenoid compounds to human albumin-containing serum in an amount of from about 0.25 wt % to about 15 wt % to cause human albumin to precipitate; and
  recovering the precipitate consisting essentially of human albumin, said albumin being substantially separated from plasma and other blood components, substantially free of stabilizers and substantially saturated with one or more glycyrrhizic triterpenoid compounds.

15. The product of the process of claim 14.

16. A method of preparing a therapeutic composition of matter consisting essentially of human serum human albumin suitable for human therapy substantially saturated with one or more glycyrrhizic triterpenoid compounds comprising the steps of:
  adding one or more glycyrrhizic triterpenoid compounds to human serum in an amount of from about 0.25 wt % to about 15 wt % to cause human albumin to precipitate; and
  recovering the precipitate consisting essentially of human serum human albumin, said albumin being substantially separated from plasma and other blood components, substantially free of stabilizers and substantially saturated with one or more glycyrrhizic triterpenoid compounds.

17. The product of the process of claim 16.

18. A method for preparing a therapeutic composition of matter consisting essentially of biologically competent, virus inactivated human albumin suitable for human therapy comprising mixing a concentrate of human albumin, said albumin being substantially separated from plasma and other blood components, substantially free of stabilizers; with one or more glycyrrhizic triterpenoid compounds, the albumin composition comprising, during preparation, an amount between 0.0001 and 10 weight percent of glycyrrhizic triterpenoid compound sufficient to inactivate pathogenic virus therein and maintaining the mixture of human albumin and glycyrrhizic triterpenoid compound at a temperature of about 37° C. for a period of at least about one hour.

19. A method for preparing a therapeutic composition of matter consisting essentially of biologically competent, virus inactivated human albumin suitable for human therapy comprising mixing a concentrate of human albumin, said albumin being substantially separated from plasma and other blood components, substantially free of stabilizers and which has not been pasteurized, with one or more glycyrrhizic triterpenoid compounds in a concentration of from 0.0001 to 10.0 wt/% based on human albumin sufficient to substantially inactivate susceptible viruses and maintaining the mixture of human albumin and glycyrrhizic triterpenoid compound at a temperature of about 37° C. for a period of at least about one hour.

20. The method of claim 19 wherein the glycyrrhizic triterpenoid compounds is present in a concentration of from about 0.05 to about 3 wt/% in the human albumin.

* * * * *